(12) United States Patent
Matula et al.

(10) Patent No.: US 11,596,869 B2
(45) Date of Patent: Mar. 7, 2023

(54) SYSTEM AND METHOD OF ADJUSTING ATTRIBUTES OF AN APPLICATION BASED AT LEAST ON A STRESS INDEX ASSOCIATED WITH A USER

(71) Applicant: Dell Products L.P., Round Rock, TX (US)

(72) Inventors: Terry Lane Matula, Austin, TX (US); Deeder M. Aurongzeb, Austin, TX (US); Ziqian Wang, Austin, TX (US)

(73) Assignee: Dell Products L.P., Round Rock, TX (US)

( * ) Notice: Subject to any disclaimer, the term of this patent is extended or adjusted under 35 U.S.C. 154(b) by 0 days.

(21) Appl. No.: 17/146,684

(22) Filed: Jan. 12, 2021

(65) Prior Publication Data
US 2022/0219085 A1    Jul. 14, 2022

(51) Int. Cl.
*A63F 13/67*    (2014.01)
*G16H 40/67*    (2018.01)
(Continued)

(52) U.S. Cl.
CPC ............ *A63F 13/67* (2014.09); *A61B 5/0205* (2013.01); *A61B 5/165* (2013.01); *A63F 13/212* (2014.09);
(Continued)

(58) Field of Classification Search
CPC ........ A63F 13/67; A63F 13/212; A63F 13/56; G16H 40/67; G06F 16/245; G06F 3/013; A61B 5/0205; A61B 5/165; G09G 5/37
See application file for complete search history.

(56) References Cited

U.S. PATENT DOCUMENTS

| 7,331,870 B2 | 2/2008 | Smith et al. |
| 8,597,109 B2 * | 12/2013 | Herrmann ............... G07F 17/32 463/16 |

(Continued)

OTHER PUBLICATIONS

Bayevsky, R. M., et al. "HRV analysts under the usage of different electrocardiography systems (Methodical recommendations)." *Committee of Clinic Diagnostic Apparatus and the Committee of New Medical Techniques of Ministry of Health of Russia* 4 (2002): 2-67.

(Continued)

*Primary Examiner* — Malina D. Blaise
(74) *Attorney, Agent, or Firm* — McDermott Will & Emery LLP

(57) ABSTRACT

In one or more embodiments, one or more systems, one or more methods, and/or one or more processes may: if historical biometric data associated with a user is available is not available, collect the historical biometric data; if the historical biometric data is available, retrieve the historical biometric data; execute an application; display at least a portion of a graphic; determine that a gaze of the user includes the at least the portion of the graphic; determine a stress index threshold associated with the user; determine a stress index associated with the user, accounting for the at least the portion of the graphic exceeding the brightness threshold; determine that the stress index has reached or exceeded the stress index threshold; provide a notification indicating that the first stress index has reached or exceeded the stress index threshold; and reduce one or more stress inducing attributes associated with the application.

20 Claims, 6 Drawing Sheets

(51) Int. Cl.
  *G06F 3/01*    (2006.01)
  *G09G 5/37*    (2006.01)
  *A61B 5/0205*  (2006.01)
  *A61B 5/16*    (2006.01)
  *A63F 13/212*  (2014.01)
  *A63F 13/56*   (2014.01)
  *G06F 16/245*  (2019.01)
  *A61B 5/024*   (2006.01)
  *A61B 5/0533*  (2021.01)
  *A61B 5/08*    (2006.01)
  *A61B 5/00*    (2006.01)

(52) U.S. Cl.
  CPC .............. *A63F 13/56* (2014.09); *G06F 3/013* (2013.01); *G06F 16/245* (2019.01); *G09G 5/37* (2013.01); *G16H 40/67* (2018.01); *A61B 5/02405* (2013.01); *A61B 5/0533* (2013.01); *A61B 5/0816* (2013.01); *A61B 5/163* (2017.08); *A61B 5/4863* (2013.01); *A61B 2503/12* (2013.01); *A63F 2300/1012* (2013.01); *A63F 2300/6027* (2013.01); *A63F 2300/6607* (2013.01); *G09G 2354/00* (2013.01)

(56) References Cited

U.S. PATENT DOCUMENTS

| | | | |
|---|---|---|---|
| 9,311,825 B2 | 4/2016 | Lusted et al. | |
| 10,835,823 B2* | 11/2020 | Sumant | A63F 13/212 |
| 10,902,243 B2* | 1/2021 | Wang | G06V 40/169 |
| 2014/0243093 A1* | 8/2014 | Rom | A63F 13/212 |
| | | | 463/43 |
| 2015/0009121 A1* | 1/2015 | Chuang | G16Z 99/00 |
| | | | 345/156 |
| 2016/0112681 A1* | 4/2016 | Kaestle | G16H 20/70 |
| | | | 348/78 |
| 2016/0262680 A1* | 9/2016 | Martucci | A61B 5/162 |
| 2017/0087470 A1* | 3/2017 | Bostick | A63F 13/35 |
| 2018/0182095 A1* | 6/2018 | Li | A61B 5/02416 |
| 2018/0293424 A1* | 10/2018 | Venkataraman | G06F 3/011 |
| 2018/0345128 A1* | 12/2018 | Ahmed | A63F 13/537 |
| 2019/0355209 A1* | 11/2019 | Sorey | G07F 17/3206 |
| 2020/0057661 A1* | 2/2020 | Bendfeldt | G06V 40/103 |
| 2020/0206631 A1* | 7/2020 | Sumant | G06V 40/20 |
| 2020/0298131 A1* | 9/2020 | Pinto | A63F 13/79 |
| 2021/0192884 A1* | 6/2021 | Idris | G06N 3/084 |
| 2021/0346806 A1* | 11/2021 | Pardeshi | A63F 13/79 |
| 2021/0357618 A1* | 11/2021 | Venkataraman | G06F 3/147 |

OTHER PUBLICATIONS

Tlija, Amira, et al. "Stress level classification using heart rate variability," *Advances in Science, Technology and Engineering Systems Journal* 4.3 (2019): 38-46.

\* cited by examiner

SYSTEM AND METHOD OF ADJUSTING ATTRIBUTES OF AN APPLICATION BASED AT LEAST ON A STRESS INDEX ASSOCIATED WITH A USER

BACKGROUND

Field of the Disclosure

This disclosure relates generally to information handling systems and more particularly to adjusting attributes of an application based at least on a stress index associated with a user.

Description of the Related Art

As the value and use of information continues to increase, individuals and businesses seek additional ways to process and store information. One option available to users is information handling systems. An information handling system generally processes, compiles, stores, and/or communicates information or data for business, personal, or other purposes thereby allowing users to take advantage of the value of the information. Because technology and information handling needs and requirements vary between different users or applications, information handling systems may also vary regarding what information is handled, how the information is handled, how much information is processed, stored, or communicated, and how quickly and efficiently the information may be processed, stored, or communicated. The variations in information handling systems allow for information handling systems to be general or configured for a specific user or specific use such as financial transaction processing, airline reservations, enterprise data storage, or global communications. In addition, information handling systems may include a variety of hardware and software components that may be configured to process, store, and communicate information and may include one or more computer systems, data storage systems, and networking systems.

SUMMARY

In one or more embodiments, one or more systems, one or more methods, and/or one or more processes may determine if historical biometric data associated with a user is available; if the historical biometric data associated with the user is not available, may collect the historical biometric data associated with the user; if the historical biometric data associated with the user is available, may retrieve the historical biometric data associated with the user from a memory medium; may execute, by at least one processor of an information handling system, an application; may display, by the application via a display, at least a portion of a graphic; may determine that the at least the portion of the graphic exceeds a brightness threshold; may determine that a gaze of the user includes the at least the portion of the graphic; may determine a first stress index threshold based at least on a baseline stress index, which is determined from multiple mean health indicators from biometric data from multiple people, and based at least on the historical biometric data associated with the user; may determine a first stress index associated with the user, accounting for the at least the portion of the graphic exceeds the brightness threshold; may determine that the first stress index associated with the user has reached or exceeded the stress index threshold; may provide, to the application, a notification indicating that the first stress index has reached or exceeded the threshold; and in response to the notification, may reduce one or more stress inducing attributes associated with the application.

In one or more embodiments, accounting for the at least the portion of the graphic exceeding the brightness threshold may include reducing numerical weight associated with a heart rate associated with the user. In one or more embodiments, the one or more systems, the one or more methods, and/or the one or more processes may further: determine the biometric data from the multiple people; determine the multiple mean health indicators from the biometric data from the plurality of people; and determine the baseline stress index from the multiple mean health indicators from biometric data from the multiple people. In one or more embodiments, the application may include a game. In one example, reducing the one or more stress inducing attributes associated with the application may include reducing one or more efficacies of one or more opponent non-player characters associated with the application. In another example, reducing the one or more stress inducing attributes associated with the application may include increasing one or more efficacies of one or more ally non-player characters associated with the application.

In one or more embodiments, the historical biometric data associated with the user may include one or more of a heart rate variation, a heart rate, a respiration rate, a galvanic skin response, electrodermal activity, a skin conductance response, a sympathetic skin response, a horizontal gaze nystagmus, a pupil dilation, an electrodermal response, a psychogalvanic reflex, and a skin conductance level. In one or more embodiments, the one or more systems, the one or more methods, and/or the one or more processes may further: determine that the first stress index associated with the user has not reached or exceeded the stress index threshold; in response to determining that the first stress index associated with the user has not reached or exceeded the stress index threshold, collect the historical biometric data associated with the user again; determine a second stress index associated with the user; determine if the second stress index associated with the user has reached or exceeded the stress index threshold; if the second stress index associated with the user has reached or exceeded the stress index threshold, provide, to the application, a second notification indicating that the second stress index has reached or exceeded the threshold; and if the second stress index associated with the user has not reached or exceeded the stress index threshold, collect the historical biometric data associated with the user again.

BRIEF DESCRIPTION OF THE DRAWINGS

For a more complete understanding of the present disclosure and its features/advantages, reference is now made to the following description, taken in conjunction with the accompanying drawings, which are not drawn to scale, and in which.

DETAILED DESCRIPTION

Figure 1A:
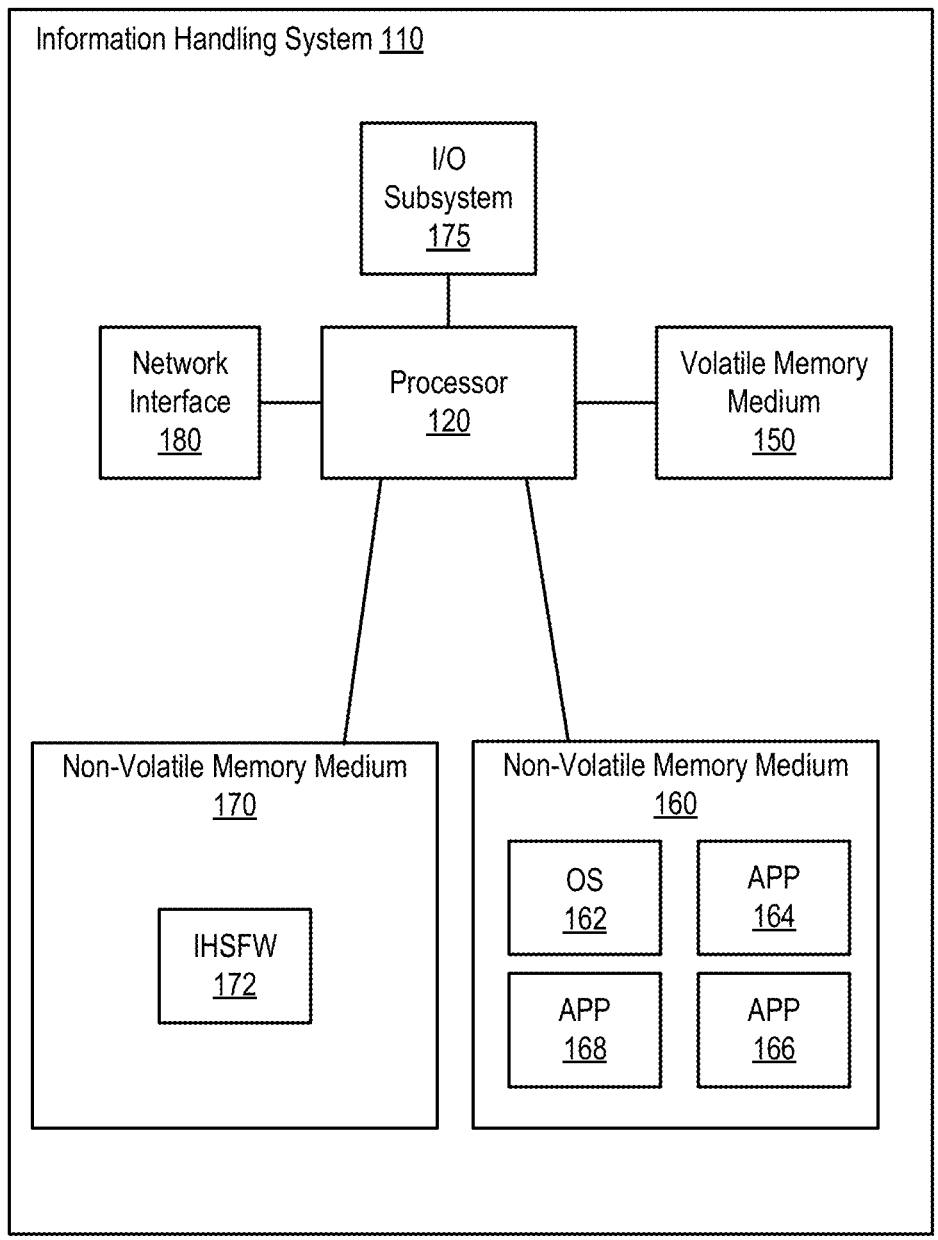
FIG. 1A illustrates an example of an information handling system, according to one or more embodiments.

In the following description, details are set forth by way of example to facilitate discussion of the disclosed subject matter. It should be apparent to a person of ordinary skill in the field, however, that the disclosed embodiments are examples and not exhaustive of all possible embodiments.

As used herein, a reference numeral refers to a class or type of entity, and any letter following such reference numeral refers to a specific instance of a particular entity of that class or type. Thus, for example, a hypothetical entity referenced by '12A' may refer to a particular instance of a particular class/type, and the reference '12' may refer to a collection of instances belonging to that particular class/type or any one instance of that class/type in general.

In one or more embodiments, video games may capture and/or may mimic one or more facets of reality. Further, more immersive gaming experiences may be developed and may be provided to users. For example, virtual reality (VR) systems may capture and/or may mimic one or more facets of reality and/or provide one or more immersive gaming experiences. In one or more embodiments, electronic sports or "e-sports" (e.g., a form of sport competition using video games) may utilize competitive biometric analysis similar to that of traditional sports. In one or more embodiments, equipment utilized with VR systems and/or augmented reality (AR) systems may be bulky and/or intrusive to users. In one or more embodiments, one or more systems, one or more methods, and/or one or more processes may utilize one or more non-invasive and/or embedded solutions for one or more incorporations of AR and/or VR.

In one or more embodiments, biometric data of a user may be remotely measured. For example, a stress level of the user may be determined based at least on the biometric data of the user. The stress level of the user may be utilized in one or more AR systems and/or one or more VR systems. In one or more embodiments, a stress index (SI) of a user may be determined based at least on biometric data associated with a user. For example, the SI associated with the user may be utilized as a proxy for actual stress associated with the user and/or emotional or autonomic response within reality-simulating games and/or a performance or burnout monitor for competitive gamers.

In one or more embodiments, multiple biometrics may be determined to determine a SI. For example, multiple biometrics may include a heart rate variation (HRV), a respiration rate (RR), a galvanic skin response (GSR), electrodermal activity (EDA), a skin conductance response (SCR), a sympathetic skin response (SSR), a horizontal gaze nystagmus (HGN), an eye gaze, pupil dilation, an electrodermal response (EDR), a psychogalvanic reflex (PGR), and a skin conductance level (SCL), among others. For instance, the HRV, the RR, the GSR, the EDA, the SCR, the SSR, the HGN, the eye gaze, the pupil dilation, the EDR, the PGR, and/or the SCL, among others, may be determined via one or more objects (e.g., a mouse, a joystick, a touchpad, a keyboard, etc.) that a user contacts and/or touches. In one or more embodiments, one or more systems, one or more methods, and/or one or more processes may utilize a process that may measure a SI from one or more of the HRV, the RR, the GSR, the EDA, the SCR, the SSR, the HGN, the eye gaze, the pupil dilation, the EDR, the PGR, and the SCL, among others, responsiveness of gaming system to autonomic feedback by user, and historical records of gamer performance and/or fatigue from one or more biometric perspectives.

In one or more embodiments, one or more systems, one or more methods, and/or one or more processes may utilize biometric collection processes to sample one or more of a HRV, a RR, a GSR, an EDA, a SCR, a SSR, a HGN, an eye gaze, a pupil dilation, an EDR, a PGR, and a SCL, among others, at a frequency. For example, the frequency may be 1 Hz. In one or more embodiments, a baseline SI of a user may be determined. For example, a first time user may relax for a first period of time (e.g., five minutes), and after the first time, biometric data of the first time user may be determined over a second period of time (e.g., one minute). In one or more embodiments, after a process begins, a biometric data sample may be compared and/or contrasted with historical biometric data (e.g., one minute of historical biometric data) in determining a SI for a user. In one or more embodiments, one or more systems, one or more methods, and/or one or more processes may utilize a modified Baevsky's algorithm.

In one or more embodiments, biometric data may be collected from multiple players. For example, biometric data may be collected from multiple players of multiple hour events such as gaming tournaments and/or training sessions for competitive gaming. For instance, performance managers may monitor relative stress levels of multiple users and/or may access historical records of the multiple users. In one or more embodiments, to provide an immersive, reality-like experience, one or more systems, one or more methods, and/or one or more processes may utilize a SI as a proxy for emotional feedback of users. For example, emotional simulation may be captured from gaming architectures, such as first person shoot (FPS) and/or horror genres. The emotional simulation may be incorporated into characters and/or avatars of a game. For instance, the characters and/or the avatars of the game may mirror user feelings onto a screen and/or may close an AR emotional feedback loop.

In one or more embodiments, tracking a stress level of a user may include tracking a SI of the user. In one or more embodiments, one or more systems, one or more methods, and/or one or more processes may utilize tracking a stress level of a user to improve a performance of the user. For example, the one or more systems, the one or more methods, and/or the one or more processes may analyze the stress level of the user to improve the performance of the user.

In one or more embodiments, a pursuit of quality in-game performance displayed by the demand for better processors and/or better graphics processing units may extend to a demand for data-driven gaming performance feedback and assessment. In one or more embodiments, integration of SI and biometrics within an information handling system and adoption of biometrics tracking in e-sports may spawn one or more of full integration of biometrics, SI available to public and emotional feedback games, among others. In one or more embodiments, one or more systems, one or more methods, and/or one or more processes may utilize a camera to determine biometric data associated with a user. For example, the camera may be configured to convert light to digital data. For instance, the camera may be configured to convert light in an infrared (IR) spectrum to digital data. As an example, the camera may be an IR camera. In one or more embodiments, one or more systems, one or more methods, and/or one or more processes may utilize photoplethysmography (PPG). For example, PPG may include an optical method and/or an optical process of detecting and/or determining volumetric changes in blood in peripheral circulation. For instance, PPG may be non-invasive. As an example, PPG may determine one or more measurements at a surface of skin of a person (e.g., a user).

In one or more embodiments, a stress level of a user may vary. For example, the stress level of the user may be high a first week and low a second week. In one or more embodiments, stress levels of a user may be stored via a memory medium. For example, stress levels of a user may be stored via database. In one or more embodiments, one or more systems, one or more methods, and/or one or more processes may determine a mean stress level of the user over a period of time. For example, a mean may be an arithmetic mean, a geometric mean, a harmonic mean, a generalized mean, a weighted arithmetic mean, a weighted geometric mean, a weighted harmonic mean, a truncated mean, and an interquartile mean, among others.

Turning now to FIG. 1A, an example of an information handling system is illustrated, according to one or more embodiments. An information handling system (IHS) 110 may include a hardware resource or an aggregate of hardware resources operable to compute, classify, process, transmit, receive, retrieve, originate, switch, store, display, manifest, detect, record, reproduce, handle, and/or utilize various forms of information, intelligence, or data for business, scientific, control, entertainment, or other purposes, according to one or more embodiments. For example, IHS 110 may be a personal computer, a desktop computer system, a laptop computer system, a server computer system, a mobile device, a tablet computing device, a personal digital assistant (PDA), a consumer electronic device, an electronic music player, an electronic camera, an electronic video player, a wireless access point, a network storage device, or another suitable device and may vary in size, shape, performance, functionality, and price. In one or more embodiments, a portable IHS 110 may include or have a form factor of that of or similar to one or more of a laptop, a notebook, a telephone, a tablet, and a PDA, among others. For example, a portable IHS 110 may be readily carried and/or transported by a user (e.g., a person). In one or more embodiments, components of IHS 110 may include one or more storage devices, one or more communications ports for communicating with external devices as well as various input and output (I/O) devices, such as a keyboard, a mouse, and a video display, among others. In one or more embodiments, IHS 110 may include one or more buses operable to transmit communication between or among two or more hardware components. In one example, a bus of IHS 110 may include one or more of a memory bus, a peripheral bus, and a local bus, among others. In another example, a bus of IHS 110 may include one or more of a Micro Channel Architecture (MCA) bus, an Industry Standard Architecture (ISA) bus, an Enhanced ISA (EISA) bus, a Peripheral Component Interconnect (PCI) bus, HyperTransport (HT) bus, an inter-integrated circuit ($I^2C$) bus, a serial peripheral interface (SPI) bus, a low pin count (LPC) bus, an enhanced serial peripheral interface (eSPI) bus, a universal serial bus (USB), a system management bus (SMBus), and a Video Electronics Standards Association (VESA) local bus, among others.

In one or more embodiments, IHS 110 may include firmware that controls and/or communicates with one or more hard drives, network circuitry, one or more memory devices, one or more I/O devices, and/or one or more other peripheral devices. For example, firmware may include software embedded in an IHS component utilized to perform tasks. In one or more embodiments, firmware may be stored in non-volatile memory, such as storage that does not lose stored data upon loss of power. In one example, firmware associated with an IHS component may be stored in non-volatile memory that is accessible to one or more IHS components. In another example, firmware associated with an IHS component may be stored in non-volatile memory that may be dedicated to and includes part of that component. For instance, an embedded controller may include firmware that may be stored via non-volatile memory that may be dedicated to and includes part of the embedded controller.

As shown, IHS 110 may include a processor 120, a volatile memory medium 150, non-volatile memory media 160 and 170, an I/O subsystem 175, and a network interface 180. As illustrated, volatile memory medium 150, non-volatile memory media 160 and 170, I/O subsystem 175, and network interface 180 may be communicatively coupled to processor 120.

In one or more embodiments, one or more of volatile memory medium 150, non-volatile memory media 160 and 170, I/O subsystem 175, and network interface 180 may be communicatively coupled to processor 120 via one or more buses, one or more switches, and/or one or more root complexes, among others. In one example, one or more of volatile memory medium 150, non-volatile memory media 160 and 170, I/O subsystem 175, and network interface 180 may be communicatively coupled to processor 120 via one or more PCI-Express (PCIe) root complexes. In another example, one or more of I/O subsystem 175 and network interface 180 may be communicatively coupled to processor 120 via one or more PCIe switches.

In one or more embodiments, the term "memory medium" may mean a "storage device", a "memory", a "memory device", a "tangible computer readable storage medium", and/or a "computer-readable medium". For example, computer-readable media may include, without limitation, storage media such as a direct access storage device (e.g., a hard disk drive, a floppy disk, etc.), a sequential access storage device (e.g., a tape disk drive), a compact disk (CD), a CD-ROM, a digital versatile disc (DVD), a random access memory (RAM), a read-only memory (ROM), a one-time programmable (OTP) memory, an electrically erasable programmable read-only memory (EEPROM), and/or a flash memory, a solid state drive (SSD), or any combination of the foregoing, among others.

In one or more embodiments, one or more protocols may be utilized in transferring data to and/or from a memory medium. For example, the one or more protocols may include one or more of small computer system interface (SCSI), Serial Attached SCSI (SAS) or another transport that operates with the SCSI protocol, advanced technology attachment (ATA), serial ATA (SATA), a USB interface, an Institute of Electrical and Electronics Engineers (IEEE) 1394 interface, a Thunderbolt interface, an advanced technology attachment packet interface (ATAPI), serial storage architecture (SSA), integrated drive electronics (IDE), or any combination thereof, among others.

Volatile memory medium 150 may include volatile storage such as, for example, RAM, DRAM (dynamic RAM), EDO RAM (extended data out RAM), SRAM (static RAM), etc. One or more of non-volatile memory media 160 and 170 may include nonvolatile storage such as, for example, a read only memory (ROM), a programmable ROM (PROM), an erasable PROM (EPROM), an electrically erasable PROM, NVRAM (non-volatile RAM), ferroelectric RAM (FRAM), a magnetic medium (e.g., a hard drive, a floppy disk, a magnetic tape, etc.), optical storage (e.g., a CD, a DVD, a BLU-RAY disc, etc.), flash memory, a SSD, etc. In one or more embodiments, a memory medium can include one or more volatile storages and/or one or more nonvolatile storages.

In one or more embodiments, network interface 180 may be utilized in communicating with one or more networks and/or one or more other information handling systems. In one example, network interface 180 may enable IHS 110 to communicate via a network utilizing a suitable transmission protocol and/or standard. In a second example, network interface 180 may be coupled to a wired network. In a third example, network interface 180 may be coupled to an optical network. In another example, network interface 180 may be coupled to a wireless network. In one instance, the wireless network may include a cellular telephone network. In a second instance, the wireless network may include a satellite telephone network. In another instance, the wireless network may include a wireless Ethernet network (e.g., a Wi-Fi network, an IEEE 802.11 network, etc.).

In one or more embodiments, network interface 180 may be communicatively coupled via a network to a network storage resource. For example, the network may be implemented as, or may be a part of, a storage area network (SAN), personal area network (PAN), local area network (LAN), a metropolitan area network (MAN), a wide area network (WAN), a wireless local area network (WLAN), a virtual private network (VPN), an intranet, an Internet or another appropriate architecture or system that facilitates the communication of signals, data and/or messages (generally referred to as data). For instance, the network may transmit data utilizing a desired storage and/or communication protocol, including one or more of Fibre Channel, Frame Relay, Asynchronous Transfer Mode (ATM), Internet protocol (IP), other packet-based protocol, Internet SCSI (iSCSI), or any combination thereof, among others.

In one or more embodiments, processor 120 may execute processor instructions in implementing at least a portion of one or more systems, at least a portion of one or more flowcharts, at least a portion of one or more methods, and/or at least a portion of one or more processes described herein. In one example, processor 120 may execute processor instructions from one or more of memory media 150, 160, and 170 in implementing at least a portion of one or more systems, at least a portion of one or more flowcharts, at least a portion of one or more methods, and/or at least a portion of one or more processes described herein. In another example, processor 120 may execute processor instructions via network interface 180 in implementing at least a portion of one or more systems, at least a portion of one or more flowcharts, at least a portion of one or more methods, and/or at least a portion of one or more processes described herein.

In one or more embodiments, processor 120 may include one or more of a system, a device, and an apparatus operable to interpret and/or execute program instructions and/or process data, among others, and may include one or more of a microprocessor, a microcontroller, a digital signal processor (DSP), an application specific integrated circuit (ASIC), and another digital or analog circuitry configured to interpret and/or execute program instructions and/or process data, among others. In one example, processor 120 may interpret and/or execute program instructions and/or process data stored locally (e.g., via memory media 150, 160, and 170 and/or another component of IHS 110). In another example, processor 120 may interpret and/or execute program instructions and/or process data stored remotely (e.g., via a network storage resource).

In one or more embodiments, I/O subsystem 175 may represent a variety of communication interfaces, graphics interfaces, video interfaces, user input interfaces, and/or peripheral interfaces, among others. For example, I/O subsystem 175 may include one or more of a touch panel and a display adapter, among others. For instance, a touch panel may include circuitry that enables touch functionality in conjunction with a display that is driven by a display adapter.

As shown, non-volatile memory medium 160 may include an operating system (OS) 162, and applications (APPs) 164-168. In one or more embodiments, one or more of OS 162 and APPs 164-168 may include processor instructions executable by processor 120. In one example, processor 120 may execute processor instructions of one or more of OS 162 and APPs 164-168 via non-volatile memory medium 160. In another example, one or more portions of the processor instructions of the one or more of OS 162 and APPs 164-168 may be transferred to volatile memory medium 150, and processor 120 may execute the one or more portions of the processor instructions of the one or more of OS 162 and APPs 164-168 via volatile memory medium 150.

As illustrated, non-volatile memory medium 170 may include information handling system firmware (IHSFW) 172. In one or more embodiments, IHSFW 172 may include processor instructions executable by processor 120. For example, IHSFW 172 may include one or more structures and/or one or more functionalities of and/or compliant with one or more of a basic input/output system (BIOS), an Extensible Firmware Interface (EFI), a Unified Extensible Firmware Interface (UEFI), and an Advanced Configuration and Power Interface (ACPI), among others. In one instance, processor 120 may execute processor instructions of IHSFW 172 via non-volatile memory medium 170. In another instance, one or more portions of the processor instructions of IHSFW 172 may be transferred to volatile memory medium 150, and processor 120 may execute the one or more portions of the processor instructions of IHSFW 172 via volatile memory medium 150.

In one or more embodiments, processor 120 and one or more components of IHS 110 may be included in a system-on-chip (SoC). For example, the SoC may include processor 120 and a platform controller hub (not specifically illustrated).

Figure 1B:
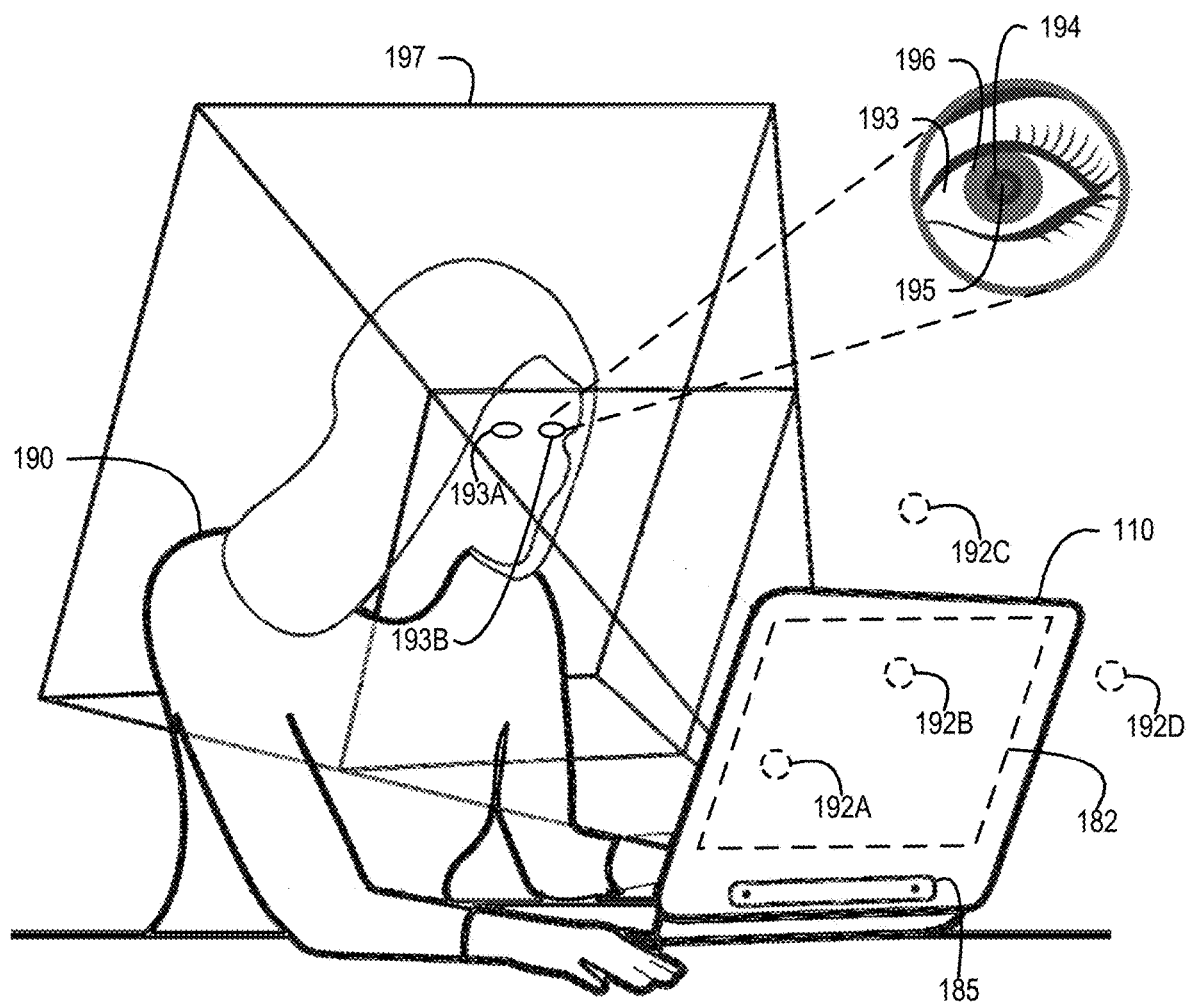
FIG. 1B illustrates an example of a user utilizing an information handling system, according to one or more embodiments.

Turning now to FIG. 1B, an example of a user utilizing an information handling system is illustrated, according to one or more embodiments. As shown, a user 190 (e.g., a person) may utilize an IHS 110. In one or more embodiments, IHS 110 may include an eye tracking device. For example, the eye tracking device may be communicatively coupled to processor 120. In one or more embodiments, one or more of camera 184 and the eye tracking device, among others, may track eyes 193A and 193B of user 190. In one example, one or more of a camera 184 (illustrated in FIG. 1C) and the eye tracking device, among others, may track a pupil 194 of an eye 193. In a second example, one or more of camera 184 and the eye tracking device, among others, may track a center 195 of a pupil 194 of an eye 193. In another example, one or more of camera 184 and the eye tracking device, among others, may track an iris 196 of an eye 193.

In one or more embodiments, one or more of eyes 193A and 193B may be illuminated. For example, IHS 110 may provide light emissions to the one or more of eyes 193A and 193B to illuminate the one or more of eyes 193A and 193B. For instance, the light emissions provided to the one or more of eyes 193A and 193B may be outside a visible spectrum of the one or more of eyes 193A and 193B. As an example, the light emissions provided to the one or more of eyes 193A and 193B may be infrared light emissions. For instance, one or more light emitting diodes (LEDs) may provide the infrared light emissions. In one or more embodiments, IHS 110 may include or be coupled to the one or more LEDs that may provide the infrared light emissions.

In one or more embodiments, one or more of camera 184 and sensors 185, among others, may be utilized in determining a location eyes 193A and 193B are with respect to a field of view 197. In one or more embodiments, a field of view of camera 184 may include field of view 197. In one or more embodiments, one or more of camera 184 and sensors 185, among others, may be utilized in determining gaze points 192A-192D. As shown, gaze points 192A and 192B may be associated with locations of display 182. As illustrated, gaze points 192C and 192D may be associated with locations that are outside display 182. In one or more embodiments, a location of user 190 with respect to field of view 197 may be determined based at least on the location eyes 193A and 193B with respect to field of view 197. In one or more embodiments, a sensor 185 may include one or more of an accelerometer, a magnetometer, a ToF device (e.g., a RADAR device, a LiDAR (light detecting and ranging) device, a SONAR (sound navigation ranging) device, etc.), an eye tracker, a proximity sensor, a temperature sensor, an ambient light sensor, a microphone, a gas sensor (e.g., a volatile organic compound sensor, a $CO_2$ sensor, an $O_2$ sensor, a carbon monoxide sensor, etc.), and an electronic gyroscope, among others.

Figure 1C:
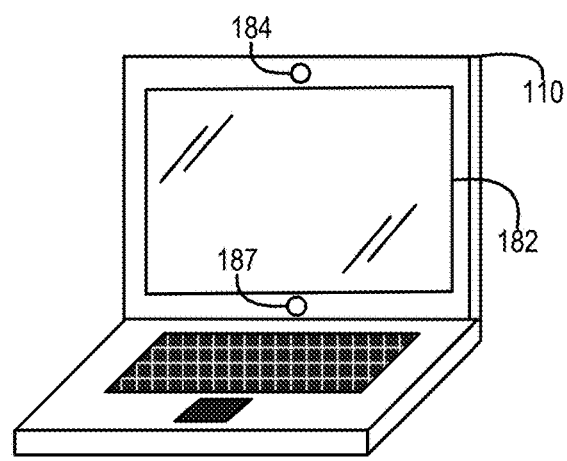
FIG. 1C illustrates a second example of an information handling system, according to one or more embodiments.

Turning now to FIG. 1C, a second example of an information handling system is illustrated, according to one or more embodiments. As shown, IHS 110 may include a camera 184. In one or more embodiments, camera 184 may be communicatively coupled to processor 120. As illustrated, IHS 110 may include a ToF sensor 187. In one or more embodiments, ToF sensor 187 may be communicatively coupled to processor 120. Although FIGS. 1B and 1C illustrate IHS 110 as including display 182, camera 184, and sensors 185, one or more of display 182, camera 184, and sensors 185, among others, may be external to IHS 110, according to one or more embodiments. For example, one or more of display 182, camera 184, and sensors 185, among others, may be coupled to IHS 110 via a wired fashion and/or one or more of display 182, camera 184, and sensors 185, among others, may be coupled to IHS 110 via a wireless fashion.

Figure 2:
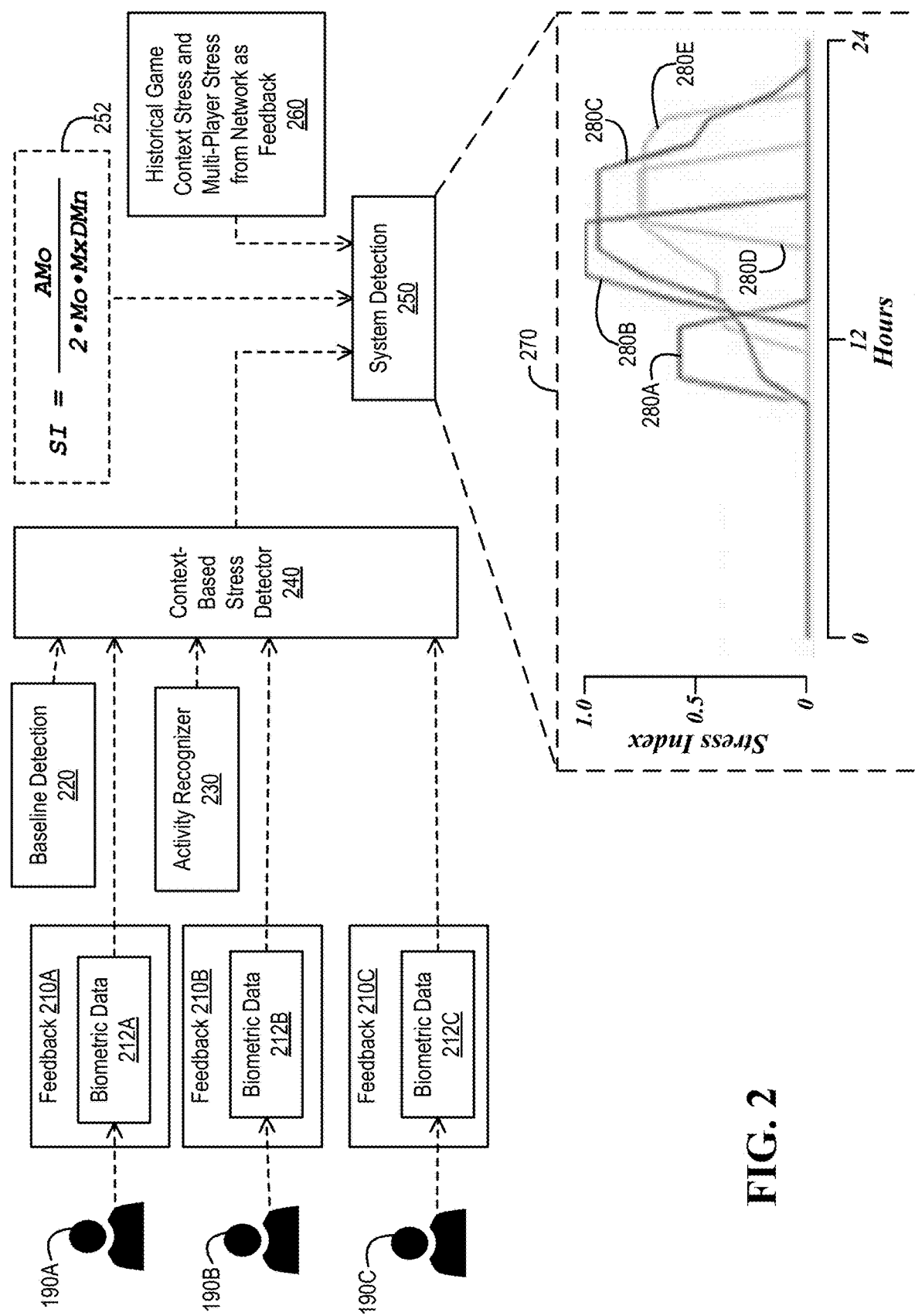
FIG. 2 illustrates an example of a stress indicator system, according to one or more embodiments.

Turning now to FIG. 2, an example of a stress indicator system is illustrated, according to one or more embodiments. In one or more embodiments, an IHS 110 may implement one or more portions of a stress indicator system. As shown, feedback 210A-210C may be respectively collected from users 190A-190C. As illustrated, feedback 210A-210C may respectively include biometric data 212A-212C. For example, biometric data 212A-212C may be respectively collected from users 190A-190C. In one or more embodiments, biometric data 212 may include one or more of a heart rate variation, a respiration rate, a galvanic skin response, electrodermal activity, a skin conductance response, a sympathetic skin response, a horizontal gaze nystagmus, an eye gaze, a pupil dilation, an electrodermal response, a psychogalvanic reflex, and a skin conductance level, among others.

In one or more embodiments, baseline detection 220 may include determining biometric data from multiple people. For example, baseline detection 220 may determine one or more means of the biometric data from the multiple people. For instance, baseline detection 220 may determine one or more baselines of health and/or one or more baselines of stress levels based at least one the one or more means of the biometric data from the multiple people. As an example, a mean of means of biometric data may be an arithmetic mean, a geometric mean, a harmonic mean, a generalized mean, a weighted arithmetic mean, a weighted geometric mean, a weighted harmonic mean, a truncated mean, and an interquartile mean, among others. In one or more embodiments, determining the one or more baselines of health and/or the one or more baselines of stress levels may include determining biometric data from the multiple people as they participate in one or more activities. For example, one or more activities may include routine office work (e.g., sitting at a desk, replying to email, etc.).

In one or more embodiments, baseline detection 220 may assign numerical values to the one or more baselines of health and/or the one or more baselines of stress levels associated with the multiple people. In one or more embodiments, a context-based stress detector 240 may receive data from biometric data 212A-212C, baseline detection 220, and activity recognizer 230, among others. As an example, biometric data 212A-212C may include one or more of a heart rate variation, a respiration rate, a galvanic skin response, electrodermal activity, a skin conductance response, a sympathetic skin response, a horizontal gaze nystagmus, a pupil dilation, an electrodermal response, a psychogalvanic reflex, and a skin conductance level, among others. In one or more embodiments, context-based stress detector 240 may provide data to a system detection 250. In one or more embodiments, system detection 250 may receive the data from context-based stress detector 240 and may receive data from a historical game context stress and multi-player stress from network as feedback 260.

In one or more embodiments, system detection 250 may utilize an equation 252 to determine a stress index, where AMo is an amplitude mode nominal index of activity of sympathetic chain regulation, Mo is a mode of presumable level of cardiovascular function, and MxDMn is a difference between maximum and minimum values of cardio intervals. For example, system detection 250 may utilize data from context-based stress detector 240 and data from historical game context stress and multi-player stress from network as feedback 260 with equation 252. In one or more embodiments, one or more of AMo, Mo, and MxDMn may be frequency domain measurements. In one or more embodiments, one or more measurements of biometric data may be determined in a frequency domain. For example, heart rate and respiration rate associated with a user 190 may be determined in a frequency domain. In one or more embodiments, a graph 270 illustrates plots 280A-280E of SI over a period of twenty-four hours. For example, plots 280A-280E of SI may be associated with multiple people. For instance, plots 280A-280C of SI may be respectively associated with users 190A-190C.

Figure 4:
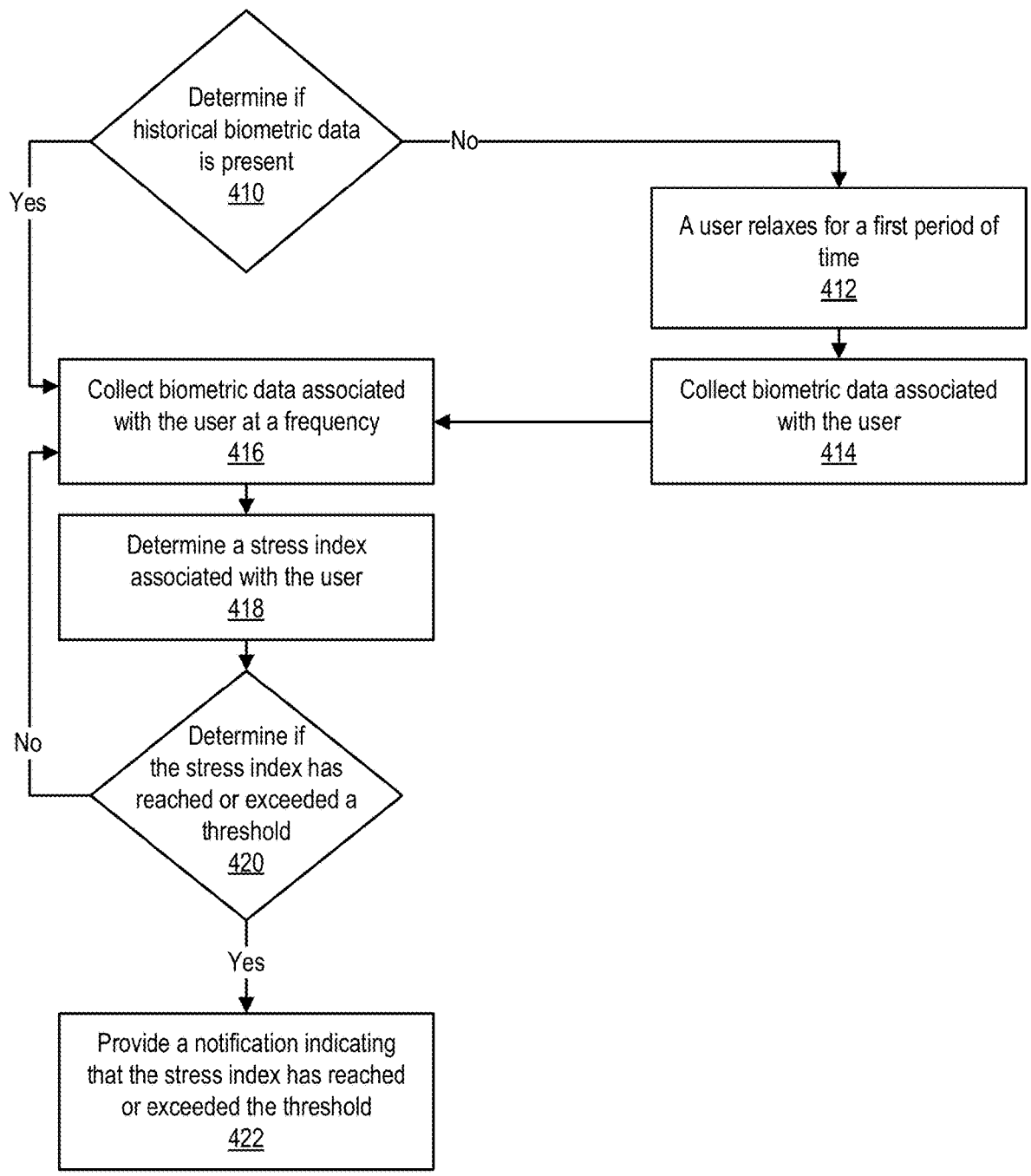
FIG. 4 illustrates an example of a method of utilizing a stress indicator system, according to one or more embodiments.

Turning now to FIG. 4, an example of a method of utilizing a stress indicator system is illustrated, according to one or more embodiments. At 410, it may be determined if historical biometric data is present. For example, it may be determined if historical biometric data associated with a user 190 is stored in a memory medium. For instance, it may be determined if historical biometric data associated with a user 190 is stored in a database. If the historical biometric data is not present, a user may relax for a period of time, at 412. For example, the user may engage in a guided meditation for a period of time.

At 414, biometric data associated with the user may be collected. For example, biometric data associated with user 190 may be collected. For instance, one or more of a heart rate variation, a respiration rate, a galvanic skin response, electrodermal activity, a skin conductance response, a sympathetic skin response, a horizontal gaze nystagmus, a pupil dilation, an electrodermal response, a psychogalvanic reflex, and a skin conductance level, among others, associated with user 190 may be collected. In one or more embodiments, collecting biometric data associated with the user may include measuring biometric data associated with the user. In one or more embodiments, the method may proceed to 416. If the historical biometric data is present, biometric data associated with the user may be collected at a frequency, at 416. For example, biometric data associated with user 190 at a frequency of 1 Hz. In one instance, the biometric data associated with user 190 may include one or more of heart rate variation, respiration rate, and galvanic skin response, among others. In another instance, the biometric data associated with user 190 may include one or more of AMo, Mo, and MxDMn, among others.

At 418, a stress index associated with the user may be determined. For example, a stress index associated with user 190 may be determined. In one or more embodiments, determining a stress index associated with the user may include determining the stress index associated with the user via equation 252. At 420, it may be determined if the stress index has reached or exceeded a threshold. If the stress index has reached or exceeded the threshold, a notification indicating that the stress index has reached or exceeded the threshold may be provided, at 422. For example, a notification indicating that the stress index has reached or exceeded the threshold may be provided to one or more listeners. For instance, the one or more listeners may be listening for one or more events, which indicate that the stress index has reached or exceeded the threshold. In one or more embodiments, a listener may include an application and/or a game. If the stress index has not reached or exceeded the threshold, the method may proceed to 416, according to one or more embodiments.

Figure 3:
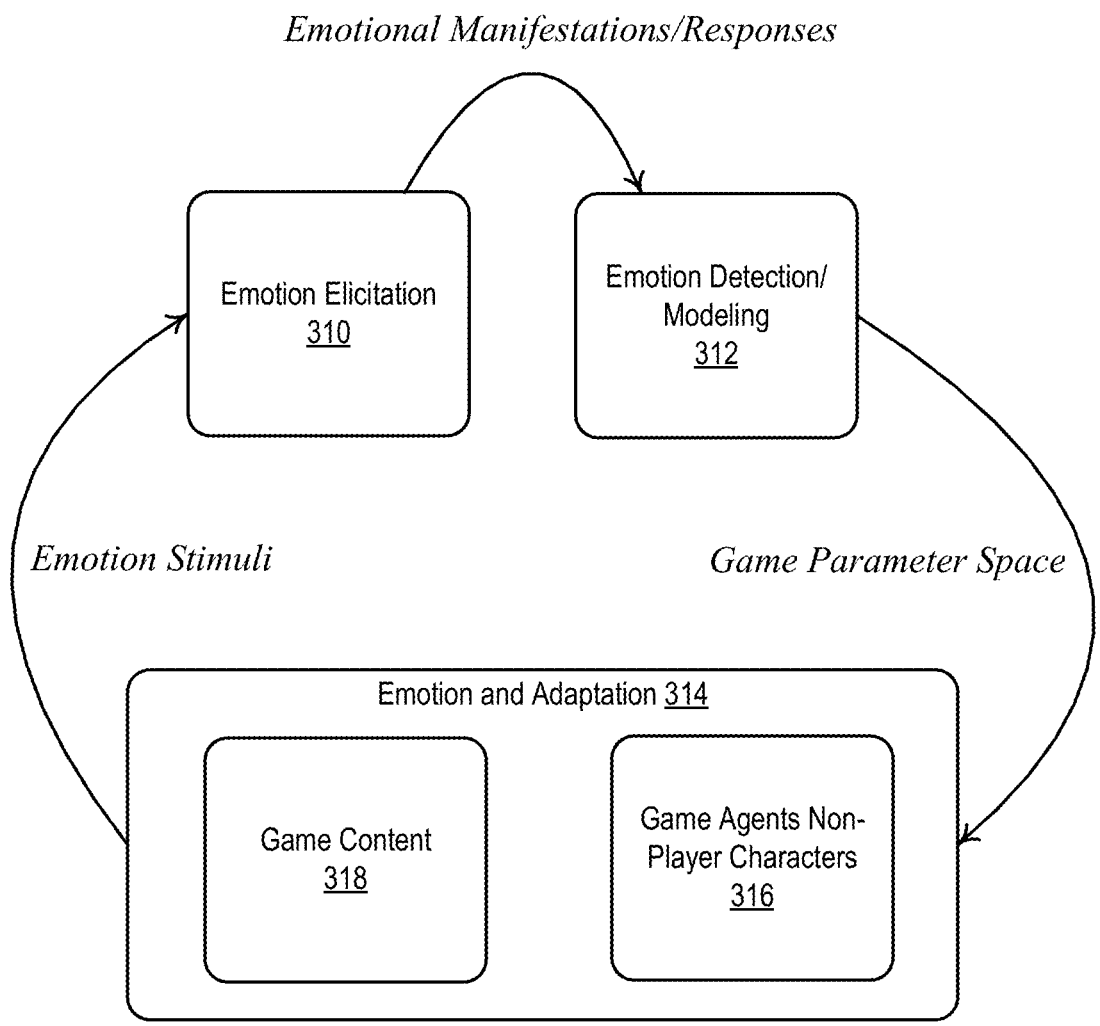
FIG. 3 illustrates an example of a method of modifying game content, according to one or more embodiments.

Turning now to FIG. 3, an example of a method of modifying game content is illustrated, according to one or more embodiments. In one or more embodiments, an emotional response may be elicited, at 310. For example, IHS 110 may elicit an emotional response from user 190. For instance, a game (e.g., an application, a program, etc.) executed by IHS 110 may elicit an emotional response from user 190. As an example, the emotional response may increase a stress index of user 190. As another example, the emotional response may decrease a stress index of user 190.

In one or more embodiments, the emotional response may be detected, at 312. For example, the emotional response may be detected via biometric data associated with user 190. In one or more embodiments, a model may be created based at least on the emotional response associated with user 190. In one or more embodiments, the game may adapt to the stress index associated with user 190, at 314. For example, the game may adapt to the stress index associated with user 190 based at least on the model associated with user 190. As an example, if the stress index associated with user 190 meets or exceeds a first threshold, the game may adapt to reduce the stress index associated with user 190. For instance, the game may reduce one or more efficacies of one or more non-player characters (NPCs) of the game, at 316. As another example, if the stress index associated with user 190 is below or meets a second threshold, the game may adapt to increase the stress index associated with user 190. For instance, the game may increase one or more efficacies of one or more NPCs of the game. In one or more embodiments, the first threshold may be different from the second threshold, or the first threshold may be the second threshold. In one or more embodiments, one or more NPCs may be one or more allies in the game. For example, the one or more allies may behave in accordance with the stress index associated with user 190. In one or more embodiments, one or more NPCs may be one or more enemies in the game. For example, the one or more enemies may behave in accordance with the stress index associated with user 190. In one or more embodiments, game content may adapt to the stress index associated with user 190, at 318.

Figure 5:
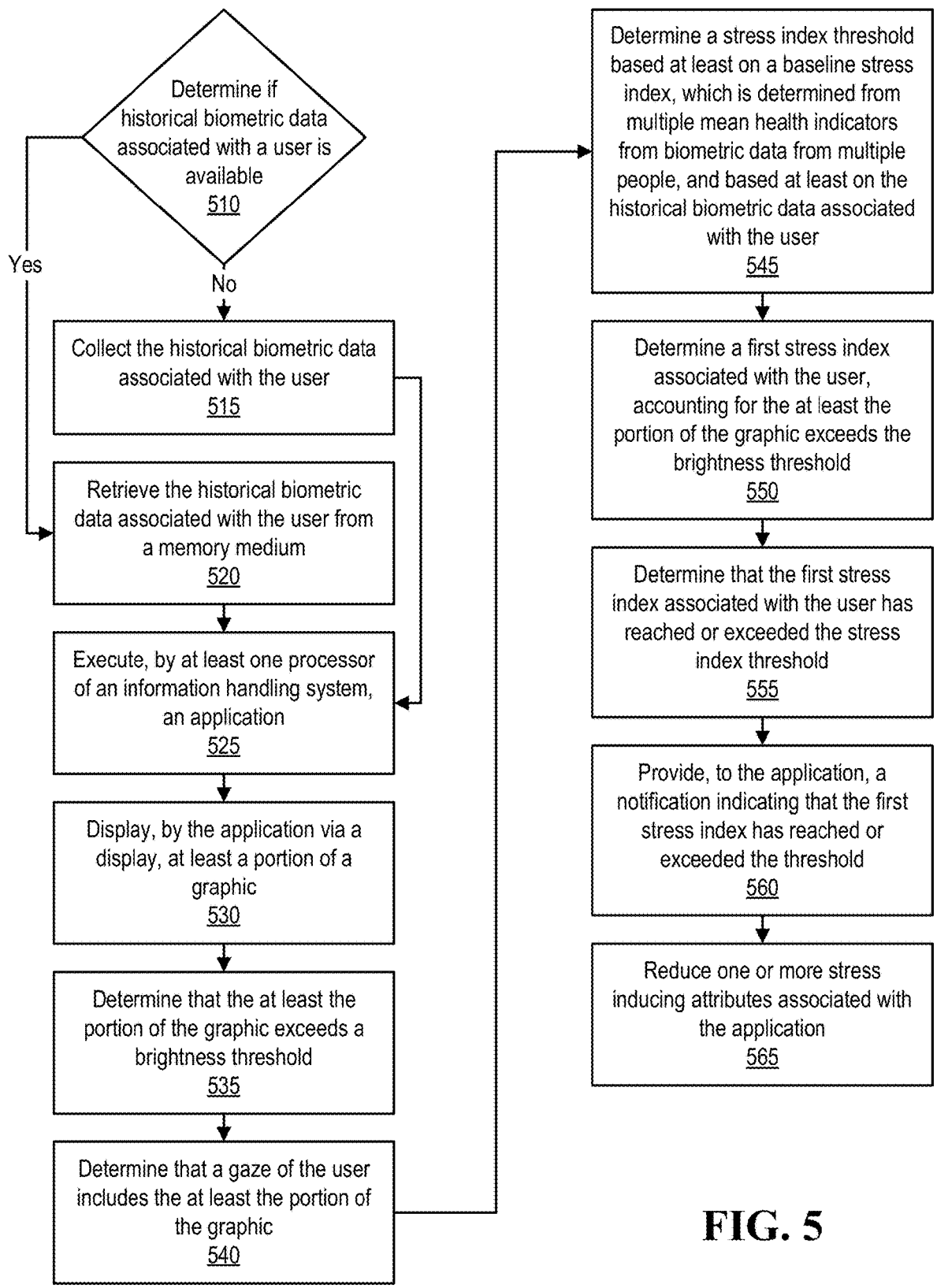
FIG. 5 illustrates an example of a method of operating an information handling system, according to one or more embodiments.

Turning now to FIG. 5, an example of a method of operating an information handling system is illustrated, according to one or more embodiments. At 510, it may be determined if historical biometric data associated with a user is available. For example, it may be determined if historical biometric data associated with a user 190 is available. In one or more embodiments, determining if the historical biometric data associated with the user is available may include searching a memory medium for the historical biometric data associated with the user. For example, determining if the historical biometric data associated with the user is available may include searching a database for the historical biometric data associated with the user.

If the historical biometric data associated with the user is not available, the historical biometric data associated with the user may be collected, at 515. In one or more embodiments, collecting the biometric data associated with the user may include measuring the biometric data associated with the user. For example, the biometric data associated with the user may be measured via one or more devices and/or one or more systems described herein. In one or more embodiments, the method may proceed to 525. If the historical biometric data associated with the user is available, the historical biometric data associated with the user may be retrieved from a memory medium. For example, the historical biometric data associated with user 190 may be retrieved from a memory medium. In one or more embodiments, retrieving the historical biometric data associated with user 190 from the memory medium may include retrieving the historical biometric data associated with user 190 from a database.

At 525, an application may be executed by at least one processor of an information handling system. For example, APP 164 may be executed by at least one processor 120 of IHS 110. In one or more embodiments, APP 164 may include a game. In one or more embodiments, APP 164 may include a first person shooter game. In one or more embodiments, APP 164 may include at least one of an AR application and a VR application, among others. For example, the at least one of the AR application and the VR application may include a first person shooter game.

At 530, at least a portion of a graphic may be displayed by the application via a display. For example, APP 164 may display at least a portion of a graphic via display 182. At 535, it may be determined that the at least the portion of the graphic exceeds a brightness threshold. For example, it may be determined that the at least the portion of the graphic exceeds a threshold number of nits. For instance, a brightness level may be measured in nits.

At 540, it may be determined that a gaze of the user includes the at least the portion of the graphic. For example, it may be determined that a gaze of user 190 includes the at least the portion of the graphic. For instance, determining that the gaze of user 190 includes the at least the portion of the graphic may include determining that user 190 is looking at the at least the portion of the graphic. As an example, determining that the gaze of user 190 includes the at least the portion of the graphic may include determining a gaze point 192 and determining that gaze point 192 intersects the at least the portion of the graphic. For instance, determining that the gaze of user 190 includes the at least the portion of the graphic may include determining gaze point 192B and determining that gaze point 192B intersects the at least the portion of the graphic.

At 545, a stress index threshold may be determined based at least on a baseline stress index, which is determined from multiple mean health indicators from biometric data from multiple people, and based at least on the historical biometric data associated with the user. In one or more embodiments, baseline detection 220 may determine a stress index threshold based at least on a baseline stress index, which is determined from multiple mean health indicators from biometric data from multiple people, and based at least on the historical biometric data associated with user 190. In one or more embodiments, baseline detection 220 may the multiple mean health indicators from the biometric data from the multiple people.

At 550, a first stress index associated with the user may be determined, accounting for the at least the portion of the graphic exceeding the brightness threshold. For example, system detection 250 may determine a first stress index associated with user 190, accounting for the at least the portion of the graphic exceeding the brightness threshold. For instance, system detection 250 may utilize equation 252 to determine the first stress index associated with user 190.

In one or more embodiments, the accounting for the at least the portion of the graphic exceeding the brightness threshold may include reducing numerical weight associated with a heart rate associated with the user. For example, the heart rate associated with the user may increase when the user observes light emissions at or above a brightness level. For instance, the increase in the heart rate associated with the user may not be indicative of a stress level. As an example, if the heart rate associated with the user increased when the user observes light emissions at or above a brightness level, an incorrect stress index or a biased stress index associated with the user may be determined. In one or more embodiments, while the heart rate associated with the user may be utilized in determining a stress index associated with the user, an influence of the heart rate associated with the user may be reduced when determining the stress index associated with the user when it is determined that the user is observing light emissions at or above a brightness level. In one example, a measurement of the heart rate associated with the user may be multiplied by a number between zero (0) and one (1) when it is determined that the user is observing light emissions at or above a brightness level. In one example, a value associated with the heart rate associated with the user may be multiplied by a number between zero (0) and one (1) when it is determined that the user is observing light emissions at or above a brightness level.

At 555, it may be determined that the first stress index associated with the user has reached or exceeded the stress index threshold. At 560, a notification indicating that the first stress index has reached or exceeded the threshold may be provided to the application. For example, a notification indicating that the first stress index has reached or exceeded the threshold may be provided to APP 164. For instance, APP 164 may be listening for the notification indicating that the first stress index has reached or exceeded the threshold. As an example, APP 164 may be listening for one or more events. For instance, at least one of the one or more events may include the notification indicating that the first stress index has reached or exceeded the threshold.

At 565, one or more stress inducing attributes associated with the application may be reduced. For example, one or more stress inducing attributes associated with APP 164 may be reduced. In one instance, reducing the one or more stress inducing attributes associated with the application may include reducing one or more efficacies of one or more opponent non-player characters associated with APP 164. In another instance, reducing the one or more stress inducing attributes associated with the application includes increasing one or more efficacies of one or more ally non-player characters associated with APP 164. In one or more embodiments, reducing one or more stress inducing attributes associated with the application may be performed in response to the notification. For example, reducing one or more stress inducing attributes associated with the application may be performed in response to receiving the notification. For instance, the application may receive the notification.

In one or more embodiments, one or more of the method and/or process elements and/or one or more portions of a method and/or a process element may be performed in varying orders, may be repeated, or may be omitted. Furthermore, additional, supplementary, and/or duplicated method and/or process elements may be implemented, instantiated, and/or performed as desired, according to one or more embodiments. Moreover, one or more of system elements may be omitted and/or additional system elements may be added as desired, according to one or more embodiments.

In one or more embodiments, a memory medium may be and/or may include an article of manufacture. For example, the article of manufacture may include and/or may be a software product and/or a program product. For instance, the memory medium may be coded and/or encoded with processor-executable instructions in accordance with at least a portion of one or more flowcharts, at least a portion of one or more systems, at least a portion of one or more methods, and/or at least a portion of one or more processes described herein to produce the article of manufacture.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. An information handling system, comprising:
 at least one processor; and
 a first memory medium, coupled to the at least one processor, that stores instructions executable by the at least one processor, which when executed by the at least one processor, cause the information handling system to:
  determine if historical biometric data associated with a user is available;
  if the historical biometric data associated with the user is not available, collect the historical biometric data associated with the user;

if the historical biometric data associated with the user is available, retrieve the historical biometric data associated with the user from a second memory medium;

execute, by the at least one processor, an application;

display, by the application via a display, at least a portion of a graphic;

determine, via a camera that converts light into digital data and that is communicatively coupled to the at least one processor, that a gaze of the user includes the at least the portion of the graphic based at least on the digital data from the camera;

determine a first stress index threshold and a second stress index threshold, based at least on a baseline stress index, which is determined from a plurality of mean health indicators from biometric data from a plurality of people, and based at least on the historical biometric data associated with the user, the second stress index threshold different from the first stress index threshold;

determine a first stress index associated with the user based at least on the digital data from the camera, including:
  determine a heart rate associated with the user, the first stress index based on the heart rate associated with the user;
  determine that at least the portion of the graphic exceeds a numerical brightness threshold;
  in response to determining that at least the portion of the graphic exceeds the numerical brightness threshold, adjust a weighting of the heart rate for the first stress index;

compare the first stress index to the first stress index threshold;

determine, based on comparing the first stress index to the first stress index threshold, that when the first stress index associated with the user has reached or exceeded the first stress index threshold:
  provide, to the application, a first notification indicating that the first stress index has reached or exceeded the first stress index threshold; and
  in response to the first notification, modify content provided by the application for display on the display by reducing one or more stress inducing attributes associated with the content provided for display by the application;

compare the first stress index to the second stress index threshold;

determine, based on comparing the first stress index to the second stress index threshold, that when the second stress index associated with the user is below or meets the second stress index threshold:
  provide, to the application, a second notification indicating that the first stress index is below or meets the second stress index threshold; and
  in response to the second notification, modify content provided by the application for display on the display by increasing one or more stress inducing attributes associated with the content provided for display by the application.

2. The information handling system of claim 1, wherein adjusting the value of the first stress index includes reducing a numerical weight associated with the heart rate associated with the user.

3. The information handling system of claim 1, wherein the instructions further cause the information handling system to:

determine the biometric data from the plurality of people;

determine the plurality of mean health indicators from the biometric data from the plurality of people; and determine the baseline stress index from the plurality of mean health indicators from biometric data from the plurality of people.

4. The information handling system of claim 1,
wherein the application includes a game; and
wherein, to reduce the one or more stress inducing attributes associated with the content provided for display by the application, the instructions further cause the information handling system to reduce one or more efficacies of one or more opponent non-player characters that are provided for display by the application.

5. The information handling system of claim 1,
wherein the application includes a game; and
wherein, to increase the one or more stress inducing attributes associated with the content provided for display by the application, the instructions further cause the information handling system to increase one or more efficacies of one or more ally non-player characters that are provided for display by the application.

6. The information handling system of claim 1, wherein the historical biometric data associated with the user includes one or more of a heart rate variation, a heart rate, a respiration rate, a galvanic skin response, electrodermal activity, a skin conductance response, a sympathetic skin response, a horizontal gaze nystagmus, a pupil dilation, an electrodermal response, a psychogalvanic reflex, and a skin conductance level.

7. The information handling system of claim 1, wherein the instructions further cause the information handling system to:

determine, based on comparing the first stress index to the first stress index threshold, that the first stress index associated with the user has not reached or exceeded the first stress index threshold;

in response to determining that the first stress index associated with the user has not reached or exceeded the first stress index threshold, collect the historical biometric data associated with the user again;

determine a second stress index associated with the user;

determine if the second stress index associated with the user has reached or exceeded the first stress index threshold;

if the second stress index associated with the user has reached or exceeded the first stress index threshold, provide, to the application, a second notification indicating that the second stress index has reached or exceeded the first stress index threshold; and if the second stress index associated with the user has not reached or exceeded the first stress index threshold, collect the historical biometric data associated with the user again.

8. A method, comprising:

determining if historical biometric data associated with a user is available;

if the historical biometric data associated with the user is not available, collecting the historical biometric data associated with the user;

if the historical biometric data associated with the user is available, retrieving the historical biometric data associated with the user from a memory medium;

executing, by at least one processor of an information handling system, an application;

displaying, by the application via a display, at least a portion of a graphic;

determining, via a camera that converts light into digital data, that a gaze of the user includes the at least the portion of the graphic based at least on the digital data from the camera;

determining a first stress index threshold and a second stress index threshold, based at least on a baseline stress index, which is determined from a plurality of mean health indicators from biometric data from a plurality of people, and based at least on the historical biometric data associated with the user, the second stress index threshold different from the first stress index threshold;

determining a first stress index associated with the user based at least on the digital data from the camera, including:

determining a heart rate associated with the user, the first stress index based on the heart rate associated with the user;

determining that at least the portion of the graphic exceeds a numerical brightness threshold;

in response to determining that at least the portion of the graphic exceeds the numerical brightness threshold, adjusting a weighting of the heart rate for the first stress index;

compare the first stress index to the first stress index threshold;

determining, based on comparing the first stress index to the first stress index threshold, that when the first stress index associated with the user has reached or exceeded the first stress index threshold:

providing, to the application, a first notification indicating that the first stress index has reached or exceeded the first stress index threshold; and in response to the first notification, modify content provided by the application for display on the display by reducing one or more stress inducing attributes associated with the content provided for display by the application;

compare the first stress index to the second stress index threshold;

determine, based on comparing the first stress index to the second stress index threshold, that when the second stress index associated with the user is below or meets the second stress index threshold:

provide, to the application, a second notification indicating that the first stress index is below or meets the second stress index threshold; and in response to the second notification, modify content provided by the application for display on the display by increasing one or more stress inducing attributes associated with the content provided for display by the application.

9. The method of claim 8, wherein adjusting the value of the first stress index includes reducing a numerical weight associated with the heart rate associated with the user.

10. The method of claim 8, further comprising:
determining the biometric data from the plurality of people;
determining the plurality of mean health indicators from the biometric data from the plurality of people; and
determining the baseline stress index from the plurality of mean health indicators from biometric data from the plurality of people.

11. The method of claim 8,
wherein the application includes a game; and
wherein the reducing the one or more stress inducing attributes associated with the content provided for display by the application includes reducing one or more efficacies of one or more opponent non-player characters that are provided for display by the application.

12. The method of claim 8,
wherein the application includes a game; and
wherein the increasing the one or more stress inducing attributes associated with the content provided for display by the application includes increasing one or more efficacies of one or more ally non-player characters that are provided for display by the application.

13. The method of claim 8, wherein the historical biometric data associated with the user includes one or more of a heart rate variation, a heart rate, a respiration rate, a galvanic skin response, electrodermal activity, a skin conductance response, a sympathetic skin response, a horizontal gaze nystagmus, a pupil dilation, an electrodermal response, a psychogalvanic reflex, and a skin conductance level.

14. The method of claim 8, further comprising:
determining, based on comparing the first stress index to the first stress index threshold, that the first stress index associated with the user has not reached or exceeded the first stress index threshold;
in response to the determining that the first stress index associated with the user has not reached or exceeded the first stress index threshold, repeating the collecting the historical biometric data associated with the user;
determining a second stress index associated with the user;
determining if the second stress index associated with the user has reached or exceeded the first stress index threshold;
if the second stress index associated with the user has reached or exceeded the first stress index threshold, providing, to the application, a second notification indicating that the second stress index has reached or exceeded the first stress index threshold; and
if the second stress index associated with the user has not reached or exceeded the first stress index threshold, repeating the collecting the historical biometric data associated with the user.

15. A computer-readable non-transitory memory medium that includes instructions that, when executed by at least one processor of an information handling system, cause the information handling system to:

determine if historical biometric data associated with a user is available;
if the historical biometric data associated with the user is not available, collect the historical biometric data associated with the user;
if the historical biometric data associated with the user is available, retrieve the historical biometric data associated with the user from a second memory medium;
execute, by the at least one processor, an application;
display, by the application via a display, at least a portion of a graphic;
determine, via a camera that converts light into digital data, that a gaze of the user includes the at least the portion of the graphic based at least on the digital data from the camera;
determine a first stress index threshold and a second stress index threshold, based at least on a baseline stress index, which is determined from a plurality of mean health indicators from biometric data from a plurality of people, and based at least on the historical biometric data associated with the user, the second stress index threshold different from the first stress index threshold;

determine a first stress index associated with the user based at least on the digital data from the camera, including:

determine a heart rate associated with the user, the first stress index based on the heart rate associated with the user;

determine that at least the portion of the graphic exceeds a numerical brightness threshold;

in response to determining that at least the portion of the graphic exceeds the numerical brightness threshold, adjust a weighting of the heart rate for the first stress index;

compare the first stress index to the first stress index threshold;

determine, based on comparing the first stress index to the first stress index threshold, that when the first stress index associated with the user has reached or exceeded the first stress index threshold:

provide, to the application, a first notification indicating that the first stress index has reached or exceeded the first stress index threshold; and in response to the first notification, modify content provided by the application for display on the display by reducing one or more stress inducing attributes associated with the content provided for display by the application;

compare the first stress index to the second stress index threshold;

determine, based on comparing the first stress index to the second stress index threshold, that when the second stress index associated with the user is below or meets the second stress index threshold:

provide, to the application, a second notification indicating that the first stress index is below or meets the second stress index threshold; and in response to the second notification, modify content provided by the application for display on the display by increasing one or more stress inducing attributes associated with the content provided for display by the application.

16. The computer-readable non-transitory memory medium of claim 15, wherein adjusting the value of the first stress index includes reducing a numerical weight associated with the heart rate associated with the user.

17. The computer-readable non-transitory memory medium of claim 15, wherein the instructions further cause the information handling system to:

determine the biometric data from the plurality of people;

determine the plurality of mean health indicators from the biometric data from the plurality of people; and determine the baseline stress index from the plurality of mean health indicators from biometric data from the plurality of people.

18. The computer-readable non-transitory memory medium of claim 15, wherein the application includes a game; and wherein, to reduce the one or more stress inducing attributes associated with the content provided for display by the application, the instructions further cause the information handling system to reduce one or more efficacies of one or more opponent non-player characters that are provided for display by the application.

19. The computer-readable non-transitory memory medium of claim 15, wherein the application includes a game; and wherein, to increase the one or more stress inducing attributes associated with the content provided for display by the application, the instructions further cause the information handling system to increase one or more efficacies of one or more ally non-player characters that are provided for display by the application.

20. The computer-readable non-transitory memory medium of claim 15, wherein the historical biometric data associated with the user includes one or more of a heart rate variation, a heart rate, a respiration rate, a galvanic skin response, electrodermal activity, a skin conductance response, a sympathetic skin response, a horizontal gaze nystagmus, a pupil dilation, an electrodermal response, a psychogalvanic reflex, and a skin conductance level.

* * * * *